United States Patent [19]
Okamura

[11] Patent Number: 5,098,407
[45] Date of Patent: Mar. 24, 1992

[54] MEDICAL PIERCING CANNULA WITH DRIP CHAMBER

[75] Inventor: Toshio Okamura, Yamanashi, Japan

[73] Assignee: Terumo Kabushiki Kaisha, Tokyo, Japan

[21] Appl. No.: 460,237

[22] Filed: Jan. 2, 1990

[30] Foreign Application Priority Data

Jan. 9, 1989 [JP] Japan .................................... 1-2282

[51] Int. Cl.[5] ......................... A61M 5/00; A61B 19/00
[52] U.S. Cl. ..................................... 604/248; 604/252; 604/405
[58] Field of Search ............... 604/251, 252, 254, 256, 604/403, 405, 406, 412, 414, 905, 126–127, 248

[56] References Cited
U.S. PATENT DOCUMENTS

| | | | |
|---|---|---|---|
| 3,092,106 | 6/1963 | Butler | 604/251 |
| 3,659,629 | 5/1972 | Deaton . | |
| 3,993,068 | 11/1976 | Forberg | 604/251 |
| 4,262,671 | 4/1981 | Kersten | 604/251 |
| 4,396,016 | 8/1983 | Becker | 604/126 |
| 4,846,637 | 7/1989 | Alderson et al. | 604/251 |
| 4,888,008 | 12/1989 | D'Alo et al. | 604/411 |
| 4,959,053 | 9/1990 | Jang | 604/411 |

FOREIGN PATENT DOCUMENTS

| | | |
|---|---|---|
| 66274 | 6/1956 | France . |
| 49-3187 | 1/1974 | Japan . |
| 50-13428 | 4/1975 | Japan . |
| 50-56096 | 5/1975 | Japan . |
| 51-63586 | 6/1976 | Japan . |
| 56-80149 | 6/1981 | Japan . |
| WO8002506 | 11/1980 | PCT Int'l Appl. . |
| A2081843 | 7/1980 | United Kingdom . |

*Primary Examiner*—C. Fred Rosenbaum
*Assistant Examiner*—Mark Bockelman
*Attorney, Agent, or Firm*—Frishauf, Holtz, Goodman & Woodward

[57] ABSTRACT

A medical piercing cannula assembly for use with a hard or soft medical container of a fluid such as a drug solution has a drip chamber a cannula having a spike at one end and engaging the drip chamber at the other end. The cannula has a fluid passage and an air passage defined therein. The fluid passage extends from said one end of the cannula and communicates with the drip chamber. The air passage extends from said one end of the cannula and communicates with atmosphere. A regulating mechanism is connected to the air passage, for regulating the rate of flow of air through the air passage.

1 Claim, 2 Drawing Sheets

MEDICAL PIERCING CANNULA WITH DRIP CHAMBER

BACKGROUND OF THE INVENTION

The present invention relates to a medical piercing cannula having a drip chamber, for use with a medical container such as a container of a fluid to be infused into a patient's body, and more particularly to a medical piercing cannula with a drip chamber, the medical piercing cannula having a fluid passage and an air passage which is associated with a regulating mechanism for regulating the rate of flow of air which enters the air passage.

When various fluids containing nutrients such as amino acids, vitamins, or the like, hemostatics, and anesthetics, and artificial blood are infused into patient's bodies by way of intravenous drip, these fluids are supplied from medical containers or bottles in which they are sealed. The fluid contained in such a medical container is introduced into a fluid conduit through a medical piercing cannula inserted into the container.

Some conventional medical piercing cannulas for use with medical containers or bottles have air passages. The medical containers of fluids with which medical piercing cannulas are used are grouped into hard containers such as glass bottles which are rigid and do not change their shape and soft containers such as fluid storage bags which are flexible and can change their shape.

When a medical piercing cannula is joined to a hard medical container in order to withdraw the contained fluid, such as a drug solution, therefrom, it is necessary to supply air through an air passage in the needle into the container so that the fluid can smoothly be evacuated from the container through replacement with the introduced air. The rate of flow of the fluid from the hard container is regulated depending on the rate of flow of air from the air passage into the hard container.

The prior medical piercing cannulas for use with medical containers are constructed such that their air passages can be closed off as desired so that they can be used with both hard and soft medical containers.

More specifically, the known medical piercing cannulas of the above type are classified into:

(1) medica piercing cannulas having air passages which can be closed off by caps or plugs in openings of the air passages;

(2) medical piercing cannulas having air passages whose openings can be adjusted in cross-sectional area by rotatable caps in the openings (see Japanese Laid-Open Utility Model Publication No. 56(1981)-80149); and (3) medical piercing cannulas having air passages with check mechanisms disposed in openings thereof (see Japanese Utility Model Publications Nos. 49(1974)-3187, 50(1975)-13428, 50(1975)-56096, and Japanese Laid-Open Patent Publication No. 51(1976)-63586).

According to the medical piercing cannulas under the category (1) above, the caps or plugs are connected to the cannulas through strings or the like so that they will not be lost after they are removed from the openings of the air passages. When such medical piercing cannulas are used, these caps or plugs tend to interfere with the user. In addition, the caps or plugs cannot smoothly be removed from or fitted into the openings.

The medical piercing cannulas of the class (2) above can be used with flexible soft containers when the air passages are closed off by turning the caps. When a medical piercing cannula of this class is used with a hard container and the cross-sectional area of the opening of the air passage is reduced by the cap, it is possible to prevent the fluid from gushing out of the hard container, but it is impossible for the user to accurately know how the fluid is being dripped. Consequently, it is difficult to regulate the rate at which the fluid is supplied from the hard container, i.e., the rate of dripping of the fluid from the hard container.

The check mechanisms associated with the air passages in the medical needles in the group (3) above are in the form of check valves. When a medical piercing cannula of this type is used with a flexible soft container, the check valve operates to prevent the fluid from flowing out of the container. One problem with these check valves is that when particles of dust or residues of the fluid are jammed in the check valve, the check valve tends to become ineffective, and the fluid in the soft container may egress from the air passage.

SUMMARY OF THE INVENTION

In view of the aforesaid drawbacks of the conventional medical piercing cannulas for use with medical containers, it is an object of the present invention to provide a medical piercing cannula having a drip chamber, which can be used with both hard and soft containers, is simple in structure, can be handled with ease, and can be manufactured inexpensively.

Another object of the present invention is to provide a medical piercing cannula having a drip infusion tube, for use with a medical container, the medical piercing cannula having a rotatable cap which is not required to be removed, attached again, or connected by a string or the like, so that the cap will not interfere with the user who uses the medical piercing cannula.

Still another object of the present invention is to provide a medical piercing cannula having a drip chamber, for use with a medical container, which medical piercing cannula prevents a fluid such as a drug solution from leaking from the medical container and can easily regulate the rate at which the fluid is supplied from the medical container, i.e., the rate of dripping of the fluid from the medical container.

A further object of the present invention is to provide a medical piercing cannula assembly for use with a medical container, comprising a drip chamber, a cannula having a spike at one end of the cannula and engaging the drip chamber at an opposite end of the cannula, the cannula having a fluid passage defined therein and extending from said one end, the fluid passage communicating with the drip chamber, and an air passage defined therein and extending from said one end, the air passage communicating with the atmosphere, and a regulating mechanism connected to the air passage, for regulating the rate of flow of air through the air passage.

A still further object of the present invention is to provide the medical piercing cannula assembly wherein the regulating mechanism comprises a cylindrical air inlet and a rotatable cap operatively coupled to the air inlet, the air inlet and the cap having respective holes, the arrangement being such that the degree of opening between the openings can be adjusted by angularly moving the cap with respect to the air inlet.

A yet further object of the present invention is to provide a medical piercing cannula assembly further including an air-permeable filter disposed in the air inlet.

The above and other objects, features and advantages of the present invention will become more apparent from the following description when taken in conjunction with the accompanying drawings in which a preferred embodiment of the present invention is shown by way of illustrative example.

DETAILED DESCRIPTION OF THE PREFERRED EMBODIMENT

Figure 1:
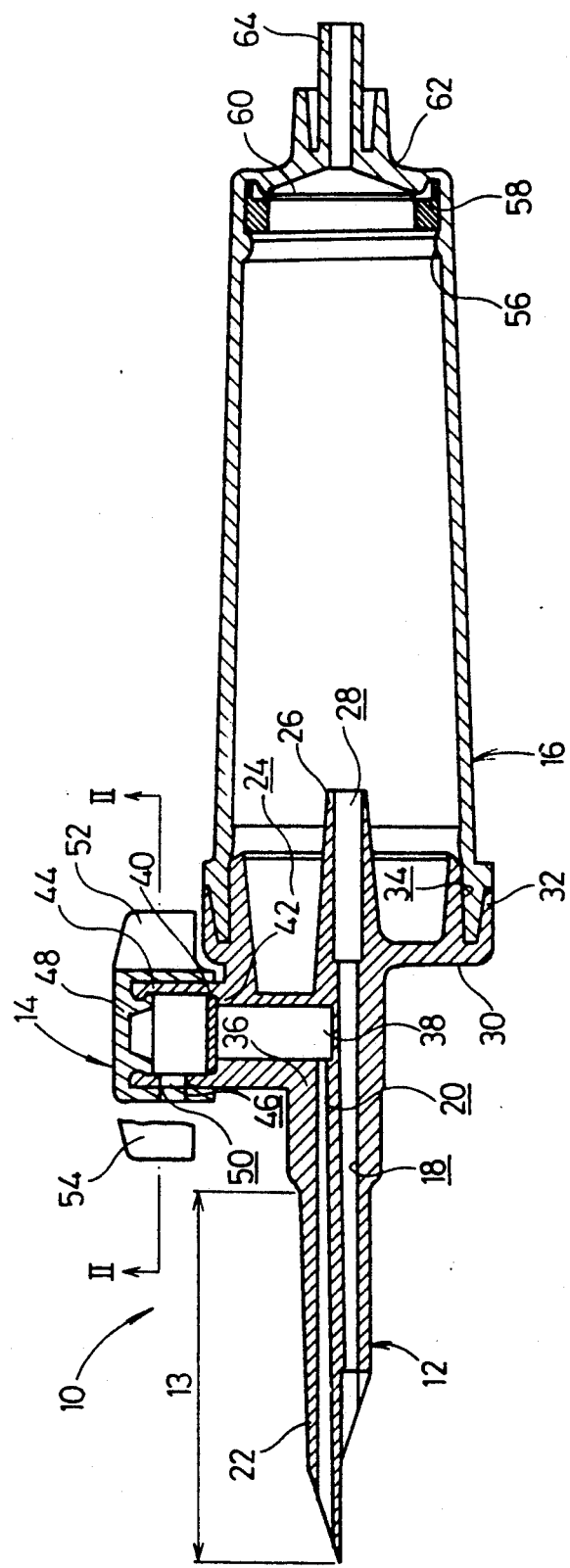
FIG. 1 is a longitudinal cross-sectional view of a medical piercing cannula with a drip chamber, according to the present invention.

As shown in FIG. 1, a medical piercing cannula assembly 10 for use with a medical container according to the present invention is basically composed of a cannula 12 having a spike 13 and an air passage 20 defined therein, a regulating mechanism 14 which selectively opens and closes the air passage 20 and regulates the opening of the air passage 20, and a drip chamber 16 attached to the proximal end of the cannula 12. The cannula 12 is preferably made of an ABS resin or polypropylene containing a filler. The drip chamber 16 is made of vinyl chloride or soft polypropylene. The cannula 12 also has a fluid passage 18 defined therein for the passage of a fluid such as a drug solution or the like therethrough into the drip chamber 16. The air passage introduces air from the regulating mechanism 14 into a medical container (not shown) to replace the fluid stored in the medical container.

The fluid passage 18 and the air passage 20 extned partially parallel to each other in the longitudinal direction of the cannula 12. The air passage 20 extends longer than the fluid passage 18 at the sharp pointed end 22 of the spike 13. The proximal end of the cannular 12, which is opposite to the pointed end thereof, has a tapered rear end 24 which extends into the drip chamber 16 and has an opening 26 communicating with the fluid passage 18. The tapered rear end 24 is positioned concentrically with the proximal end 30 of the cannula 12. The proximal end 30 has a substantially annular wall 32 which has an annular groove 34 defined therein. A tapered end of the drip chamber 16 is fitted in the annular groove 34 and fixed therein by an adhesive or ultrasonic welding.

The regulating mechanism 14 is oriented perpendicularly to the longitudinal direction of the cannular 12. The regulating mechanism 14 has an annular wall 36 which defines therein a passage 38 of a relatively large diameter that is held in communication with the air passage 20. An air-permeable filer 40 is mounted on a step 42 defined in the annular wall 36 in closing relation to the passage 38. The filer 40 is made of a water repellent material, i.e., a hydrophobic material, which will not swell or not pass water upon contact with water. Preferably, the filter 40 is made of glass fibers coated with polytetrafluoroethylene. As shown in FIG. 1, the passage 38 is much larger in diameter than the air passage 20 so that even if a fluid flows from the air passage 20 into the passage 38, the fluid remains in the passage 38 and does not fill up (clog) the passage 38.

The annular wall 36 includes an upper cylindrical air inlet 44 having a relatively small wall thickness, the air inlet 44 defining therein a radially extending hole 46. A cap 48 is rotatably fitted over the air inlet 44 and has a radially extending hole 50 which is aligned with the hole 46 in the axial direction of the air inlet 44. The rotatable cap 48 has a pair of grips 52, 54 extending radially outwardly. The hole 50 is slightly angularly displaced from the grip 54.

The drip chamber 16 has a ring-shaped embossed ridge 56 disposed on the inner wall surface thereof at the end remote from the tapered end thereof. A filter screen holder 58 on which a filter screen 60 is mounted in the end of the drip chamber 16 against the embossed ridge 56. The drip chamber 16 has a bottom 62 at the end thereof, the bottom 62 having a slanted inner surface. The bottom 62 has an outlet port 64 defined centrally therein and extending axially outwardly. The outlet port 64 will be connected to a tube or the like (not shown).

Operation of the medical piercing cannula assembly 10 thus constructed will be described below.

Figure 3:
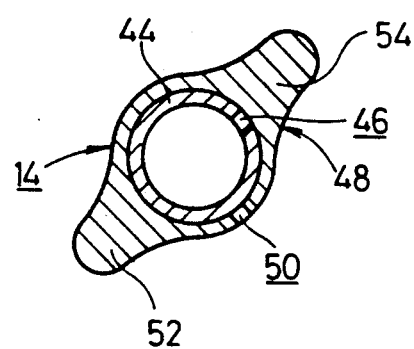
FIGS. 3 and 4 are views similar to FIG. 2, showing different angular positions of the regulating mechanism.

When the medical piercing cannula assembly 10 is used with a soft container of a fluid such as a drug solution, it is not necessary to send air into the container to replace the fluid since the drug can be forced out of the container under atmospheric pressure. Therefore, as shown in FIG. 3, the cap 48 of the regulating mechanism 14 is turned to bring the holes 46, 50 out of registry with each other until the passages 20, 38 are blocked from the atmosphere. Then, the spike 13 is inserted into the soft container. The fluid in the container then flows through the fluid passage 18 into the drip chamber 16, from which it flows out through the outlet port 64. At this time, the fluid passes through the filter screen 60 which filters out any solid particles such as a sediment from the fluid introduced from the fluid passage 18 into the drip chamber 16. The fluid which is discharged from the outlet port 64 is therefore free of undesirable solid particles. The filter screen 60 can filter out solid particles from the fluid irrespective of whether the fluid is supplied from a soft container or a hard container.

Figure 2:
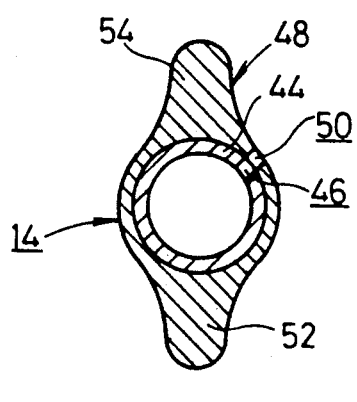
FIG. 2 is a cross-sectional view taken along line II—II of FIG. 1, showing a regulating mechanism.
Figure 4:
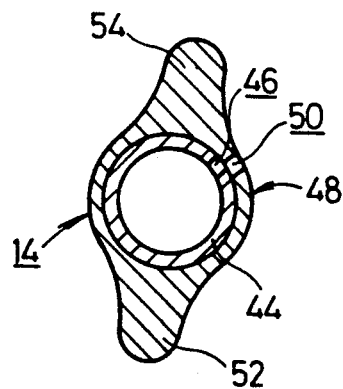

To use the medical piercing cannula assembly 10 in combination with a hard container, the cap 48 is first oriented as shown in FIG. 3. More specifically, the cap 48 is angularly displaced with the grips 52, 54 to bring the holes 46, 50 out of registry with each other, thereby blocking the passages 20, 38 from the atmosphere. Then, the pointed end 22 of the spike 13 is inserted into the hard container. The cap 48 is turned with the grips 52, 54 to bring the passages 20, 38 into communication with the atmosphere while the holes 46, 50 are being slightly displaced out of full registry, but held in communication, with each other (See FIG. 4). The cross-sectional area of the opening through which the holes 46, 50 communicate with each other can be adjusted when the cap 48 is turned, based on the rate at which the fluid drips into the drip chamber 16. Thus, the rate of flow of the fluid from the container into the drip chamber 16 can be regulated by adjusting the cross-sectional area of the opening between the holes 46, 50. When the holes 46, 50 are in full registry with each other, i.e., through 100% opening, as shown in FIG. 2, the fluid flows from the hard container into the drip chamber 16 at a maximum rate.

The medical piercing cannula assembly 10 of the present invention can therefore be used in combination with either a soft container or a hard container simply by turning the cap 48 of the regulating mechanism 14 with the grips 52, 54. Since the cap 48 is not required to be connected to the piercing cannula assembly 10 by a string or the like or to be detached from the piercing cannula assembly 10, the cap 48 does not interfere with the user of the piercing cannula assembly 10, or will not be lost. The rate at which the fluid flows from a container, especially a hard container, can easily be regulated when the cap 48 is angularly moved. It is also possible to close off the passages 20, 38 when the cap 48 is turned until the holes 46, 50 are displaced out of registry with each other. Consequently, when the medical piercing cannula assembly 10 is used with a soft container, the passages 20, 38 are fully closed to prevent the fluid from leaking out therethrough, and no solid particles in the fluid are jammed in a check valve or the like which would otherwise be employed.

Since the drip chamber 16 is made of vinyl chloride or soft polypropylene, as described above, the drip chamber 16 may be manually squeezed and released repeatedly, i.e., pumped, to force the fluid out of the outlet port 64.

With the present invention, as described above, when the medical piercing cannula assembly is to be used in combination with a hard medical container, the air passage is opened by the regulating mechanism. The rate at which the fluid is supplied from the container into the drip chamber through the fluid passage can be regulated when the opening of the air passage is adjusted with the regulating mechanism while visually observing the interior of the drip chamber. When the medical piercing cannula assembly is to be used with a soft medical container, the air passage is closed with the regulating mechanism so that the fluid in the container will not leak out through the air passage. Irrespective of whether the medical piercing cannula assembly is used with a hard or soft medical container, the cap is not required to be detached from the medica piercing cannula assembly or connected to the medical piercing cannula assembly by a string or the like, so that the cap will not be lost or does not interfere with the user of the piercing cannula assembly. The rate at which the fluid flows from a container into the drip chamber through the fluid passage can be regulated when the cap is angularly moved. Therefore, the rate of dripping of the fluid supplied into the drip chamber can easily be regulated.

As no solid particles can be jammed in a check valve which would otherwise be employed, the fluid will not leak out through the check valve.

Although a certain preferred embodiment has been shown and described, it should be understood that many changes and modifications may be made therein without departing from the scope of the appended claims.

What is claimed is:

1. A medical piercing cannula assembly for use with a medical container, comprising:

a drip chamber;

a cannula having first and second end portions;

a spike formed at said first end portion of said cannula;

said cannular engaging said drip chamber at said second end portion thereof;

said cannular further having:

a fluid passage extending from said first end portion, said fluid passage communicating with said drip chamber; and an air passage extending from said first end portion, said air passage communicating with the atmosphere; and a regulating mechanism coupled to said air passage, for regulating the flow of air through said air passage, said regulating mechanism comprising:

an annular wall which defines therein a cylindrical cavity portion having a preselected internal diameter, and a cylindrical air inlet portion communicating with said cylindrical cavity portion, said cylindrical air inlet portion having:

an internal diameter greater than said preselected internal diameter of said cylindrical cavity portion, thereby defining a step between said air inlet portion and said cylindrical cavity portion;

a disk-shaped filter disposed on said step, said filter being formed of a material that is air-permeable and hydrophobic;

a rotatable cap operatively coupled to said cylindrical air inlet portion; and at least one air hole respectively formed in each of said cap and said cylindrical air inlet portion such that rotation of said rotatable cap relative to said cylindrical air inlet portion controls the relative alignment of said holes, thereby controlling air inflow into said air passage.

* * * * *

UNITED STATES PATENT AND TRADEMARK OFFICE
CERTIFICATE OF CORRECTION

PATENT NO. : 5,098,407
DATED : March 24, 1992
INVENTOR(S) : OKAMURA, Toshio

It is certified that error appears in the above-identified patent and that said Letters Patent is hereby corrected as shown below:

Title page, section [56] References Cited, under "Foreign Patent Documents" change "WO8002506    11/1980    PCTInt'l Appl." to read
    --WO-A-8  002 506    11/1980    Germany--

WO-A-8  002 506    11/1980    Germany

Column 1, line 47, replace "medica" with --medical--.

Column 3, line 62, replace "filer" with --filter--.

Column 6, line 15 (claim 1), replace "cannular" with --cannula--.

Column 6, line 17 (claim 1), replace "cannular" with --cannula--.

Signed and Sealed this

Twelfth Day of October, 1993

Attest:

BRUCE LEHMAN

*Attesting Officer*    *Commissioner of Patents and Trademarks*